(12) United States Patent
Roberts

(10) Patent No.: US 11,944,474 B2
(45) Date of Patent: Apr. 2, 2024

(54) GUIDANCE DURING X-RAY IMAGING

(71) Applicant: KONINKLIJKE PHILIPS N.V., Eindhoven (NL)

(72) Inventor: Johannes Hendrik Roberts, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 338 days.

(21) Appl. No.: 17/288,990

(22) PCT Filed: Oct. 31, 2019

(86) PCT No.: PCT/EP2019/079794
§ 371 (c)(1),
(2) Date: Apr. 27, 2021

(87) PCT Pub. No.: WO2020/089376
PCT Pub. Date: May 7, 2020

(65) Prior Publication Data
US 2021/0401382 A1 Dec. 30, 2021

(30) Foreign Application Priority Data

Oct. 31, 2018 (EP) .................................... 18203743

(51) Int. Cl.
*A61B 6/08* (2006.01)
*A61B 6/00* (2006.01)
(Continued)

(52) U.S. Cl.
CPC .............. *A61B 6/08* (2013.01); *A61B 6/0407* (2013.01); *A61B 6/4441* (2013.01); *H04N 23/53* (2023.01)

(58) Field of Classification Search
CPC ....... A61B 6/08; A61B 6/0407; A61B 6/4441; A61B 2017/00216; A61B 2034/2048;
(Continued)

(56) References Cited

U.S. PATENT DOCUMENTS

2003/0091156 A1   5/2003   Crain
2003/0151563 A1   8/2003   Kulas
(Continued)

FOREIGN PATENT DOCUMENTS

JP    2011104031 A    6/2011
JP    2011167295 A    9/2011
(Continued)

OTHER PUBLICATIONS

International Search Report and Written Opinion of PCT/Ep2019079794, dated Dec. 6, 2019.

*Primary Examiner* — Kiho Kim

(57) ABSTRACT

The present invention relates to user guiding during X-ray imaging. In order to provide further guidance during X-ray imaging, a guiding device (10) for visual guidance during X-ray imaging is provided. The guiding device (10) comprises a camera arrangement (12), a display arrangement (14) and a housing structure (16). The housing structure comprises a housing (18) of an X-ray imaging system for housing an X-ray source or an X-ray detector. Further, the camera arrangement is configured to capture image data of a region of interest of a subject in front of the housing. Furthermore, the display arrangement is configured to present the captured image data as a live presentation of the region of interest. Still further, the camera arrangement is mounted to the housing on a first side (20) of the housing, and the display arrangement is mounted to the housing on a second side (22) of the housing, the second side being at least one of the group of lateral and opposite to the first side. Hence, the display arrangement is configured to provide a
(Continued)

presentation comprising live images from the first side to a user located on the second side of the housing.

16 Claims, 3 Drawing Sheets

(51) Int. Cl.
*A61B 6/04* (2006.01)
*H04N 23/53* (2023.01)

(58) Field of Classification Search
CPC .... A61B 2034/2051; A61B 2034/2055; A61B 2090/368; A61B 2090/372; A61B 6/465; A61B 90/36; A61B 2090/371; A61B 2090/376; A61B 6/547; A61B 6/464; A61B 6/462; A61B 6/463; H04N 23/53
See application file for complete search history.

(56) References Cited

U.S. PATENT DOCUMENTS

| | | |
|---|---|---|
| 2010/0289899 A1 | 11/2010 | Hendron |
| 2016/0174918 A1 | 6/2016 | Wang |
| 2016/0278731 A1 | 9/2016 | Babic |
| 2017/0020469 A1 | 1/2017 | Lee |
| 2018/0235555 A1 | 8/2018 | Shealy |
| 2021/0212644 A1* | 7/2021 | Glatz .................... A61B 6/487 |

FOREIGN PATENT DOCUMENTS

| | | | |
|---|---|---|---|
| WO | 2012063181 A1 | 5/2012 | |
| WO | 2014027312 A1 | 2/2014 | |
| WO | 2017077652 A1 | 5/2017 | |
| WO | 2017157715 A1 | 9/2017 | |
| WO | WO-2020025110 A1 * | 2/2020 | ............... A61B 6/04 |

* cited by examiner

GUIDANCE DURING X-RAY IMAGING

CROSS-REFERENCE TO PRIOR APPLICATIONS

This application is the U.S. National Phase application under 35 U.S.C. § 371 of International Application No. PCT/EP2019/079794, filed on Oct. 31, 2019, which claims the benefit of European Patent Application No. 18203743.2, filed on Oct. 31, 2018. These applications are hereby incorporated by reference herein.

FIELD OF THE INVENTION

The present invention relates to a guiding device for visual guidance during X-ray imaging, to an X-ray imaging system with visual user guidance during X-ray imaging and to a method for guiding a user during X-ray imaging.

BACKGROUND OF THE INVENTION

During medical examinations or interventions, X-ray imaging is used to acquire X-ray image data of the subject. For navigation, for example, live fluoroscopy X-ray images are combined with pre-acquired X-ray images, like roadmaps. Further, for planning purposes, X-ray images can be overlaid to camera images. For example, WO 2017/157715 describes the use of optical camera images overlaid with planned positions of an instrument for planning purposes and providing this on monitor units. However, it has been shown that an increasing demand exists for providing guiding information to a user.

SUMMARY OF THE INVENTION

There may thus be a need to provide further guidance during X-ray imaging.

The object of the present invention is solved by the subject-matter of the independent claims; further embodiments are incorporated in the dependent claims. It should be noted that the following described aspects of the invention apply also for the guiding device for visual guidance during X-ray imaging, for the X-ray imaging system with visual user guidance during X-ray imaging and for the method for guiding a user during X-ray imaging.

According to the present invention, a guiding device for visual guidance during X-ray imaging is provided. The guiding device comprises a camera arrangement, a display arrangement and a housing structure. The housing structure comprises a housing of an X-ray imaging system for housing an X-ray detector. The camera arrangement is configured to capture image data of a region of interest of a subject in front of the housing. Further, the display arrangement is configured to present the captured image data as a live presentation of the region of interest. Still further, the camera arrangement is mounted to the housing on a first side of the housing and the display arrangement is mounted to the housing on a second side of the housing, the second side being lateral and/or opposite to the first side. The display arrangement is configured to provide a presentation comprising live images from the first side to a user located on the second side of the housing.

This results in that the X-ray imaging system can remain in position, for example, when needed only shortly afterwards. By the camera-display arrangement, the user is provided with sufficient additional guidance during X-ray imaging as he/she can at least partly "see through" the housing. In other words, image data may be displayed on a side of the detector housing that faces the user, the image data representing a view on a scene that is located 'behind' the detector housing as seen from the user's point of view.

For example, during a medical intervention, the display arrangement may provide a physician with a live image of his hands, while a direct view on his hands is blocked by the detector housing. Thus, a need to temporarily move the detector out of the way, in order to obtain a direct view on an area of interest of the patient, is eliminated or at least reduced.

According to an example, the housing is a flat detector housing and the display arrangement comprises at least one flat display. The at least one flat display is i) mounted on the housing, or ii) integrated in the outer part of the housing. For example, display surfaces can be integrated in the housing structure.

According to an example, the camera arrangement comprises at least one optical camera mounted to the housing. Further, the display arrangement comprises at least one display comprising at least one of the group of an LCD screen, an LED screen and an OLED screen.

According to an example, it is further provided a user position detection arrangement and a processing unit. The position detection arrangement is configured to determine a spatial position of a user in relation to the housing. Further, the processing unit is configured to adapt the presentation based on the spatial position such that the presentation provides image data to the user of a situation hidden by the housing in the user's view.

According to the present invention, also an X-ray imaging system with visual user guidance during X-ray imaging is provided. The system comprises an X-ray source, an X-ray detector, a support structure and a guiding device for visual guidance during X-ray imaging according to one of the preceding examples. The X-ray source and the X-ray detector are carried by the support structure. The X-ray detector is arranged in the housing structure of the guiding device. Further, the first side of the housing is facing towards the X-ray source.

According to an example, the housing is provided with display segments on lateral facing surface portions. In an option, the display segments cover at least half of the housing's lateral facing surface portions. For example, 80% are covered with display segments. Preferably, the display segments follow the contour of the housing.

The term "lateral" relates to sidewardly facing surfaces in relation to a main viewing or detection direction of the detector or a main radiation direction of the source.

According to an example, the display is configured to display image data from the X-ray imaging overlaid to the presentation comprising live images from the first side.

This may be provided in addition to a further, main display device on which the X-ray image data is shown. The overlaid image on the detector housing provides the user, e.g. a physician not only with visual information about the scenery that he/she does not see due to the detector covering the direct line of sight. This also provides visual information about an interior of a subject, e.g. a vascular structure or a tissue/bone structure.

According to an example, the X-ray imaging system is a mobile system comprising a base with wheels. The movable C-arm is movably mounted to the base.

According to an example, a plurality of cameras mounted to the housing is provided. Further, also a spatial tracking arrangement is provided that is configured to determine a spatial relation between a user and a subject of interest. The spatial tracking arrangement is also configured to determine a user viewing direction. The spatial tracking arrangement is further configured to define a region of the subject of interest where a direct view is blocked by the housing. The spatial tracking arrangement is still further configured to select at least one of the plurality of cameras that has a viewing direction that has a largest degree of similarity with the determined user viewing direction. In other words, it is detected which camera comes close to the viewing direction of the user in order to support the impression of a see-though detector housing.

According to the present invention, also a method for guiding a user during X-ray imaging is provided. The method comprises the following steps:

a) capturing image data of a region of interest of a subject in front of the housing with a camera arrangement mounted to a first side of a housing of a housing structure; wherein the housing is a housing of an X-ray detector of an X-ray imaging system; and b) presenting the image data as a live presentation of the region of interest with a display arrangement mounted to a second side of the housing, the second side being lateral and/or opposite to the first side; wherein a presentation is provided to a user on the second side of the housing, which presentation comprises live images from the first side.

According to an aspect, a housing of an imaging device, such as a flat detector, is provided with screens or displays on which images are provided to the user that show what's on the other side of the housing. Therefore, the housing is provided with one or more cameras to provide the respective image data, e.g. live images. The cameras thus provide what would be seen by the user on the other side if the housing would not be present. The displays are provided directly on the housing such that an impression of a transparent housing is provided to the user. The housing is thus transferred from an opaque and non-transparent obstacle into an at least partially transparent housing in the user's perception.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
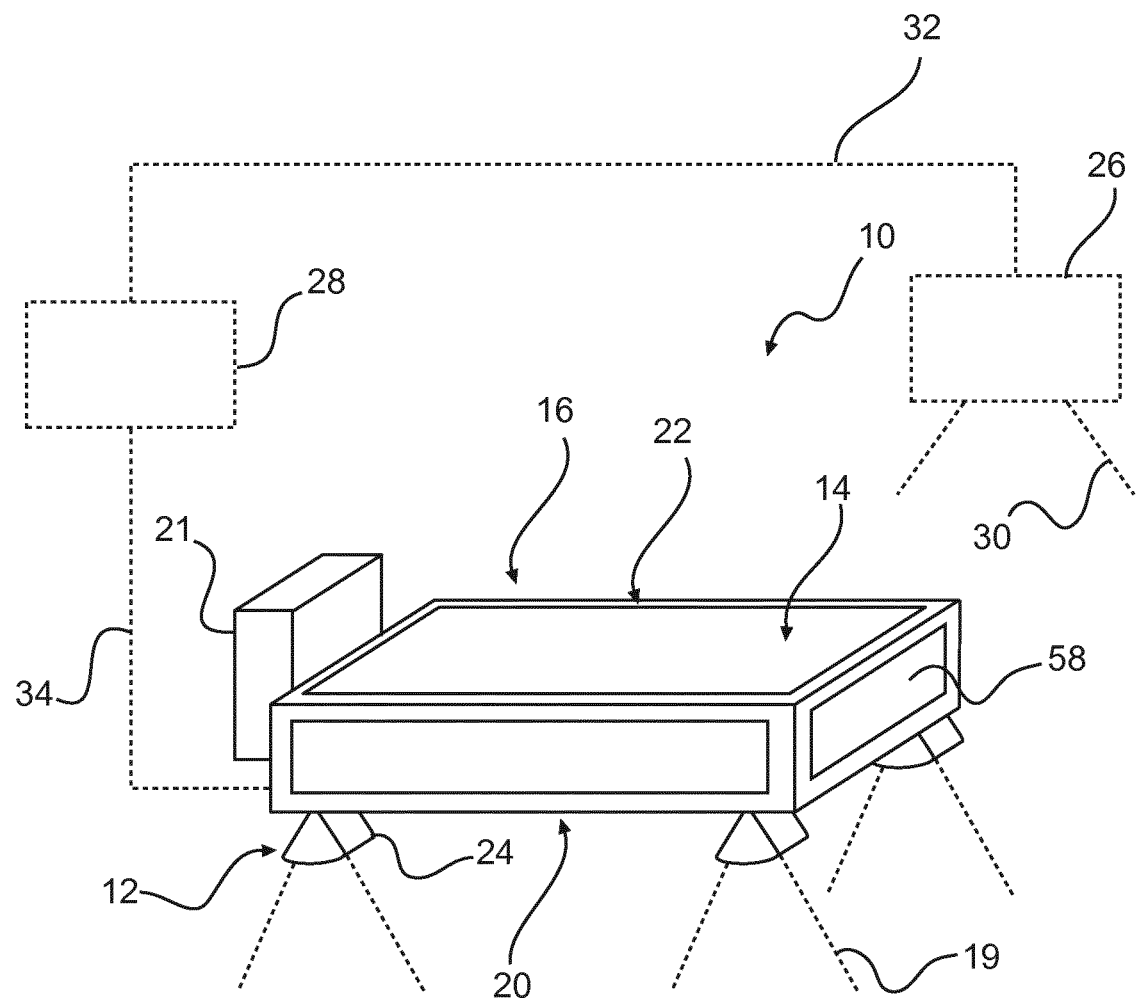
FIG. 1 schematically shows an example of a guiding device for visual guidance during X-ray imaging.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

FIG. 1 schematically shows an example of a guiding device 10 for visual guidance during X-ray imaging. The guiding device 10 comprises a camera arrangement 12, a display arrangement 14 and a housing structure 16. The housing structure 16 comprises a housing 18 of an X-ray imaging system for housing an X-ray detector. The camera arrangement 12 is configured to capture image data of a region of interest of a subject in front of the housing. The image capturing is indicated with hashed lines 19. The display arrangement 14 is configured to present the captured image data as a live presentation of the region of interest. The camera arrangement 12 is mounted to the housing 18 on a first side 20 of the housing and the display arrangement 14 is mounted to the housing at least on a second side 22 of the housing, the second side being lateral and/or opposite to the first side. The display arrangement 14 is configured to provide a presentation comprising live images from the first side to a user located on the second side of the housing.

The term "in front of" relates to a region that the first side is facing.

The camera-display arrangement thus provides visibility for the scenery on the other side of the housing. The camera-display arrangement hence provides visual information of what is blocked by the housing, for example when the user is a physician who is performing an interventional procedure and X-ray radiation is needed. The housing may hinder the direct view of the user to the region of interest of the subject, but the camera-display arrangement replaces that direct view by providing the live presentation. The camera-display arrangement provides additional information in an intuitive way, since the detector with its image presentation is so-to-speak invisible for the user as he/she can "see through".

The housing 18 is shown with a sidewardly attached holding part 21. In further examples, other attachments are provided, for example on the upper part in the middle. In such case, the part of the display arrangement 14 on top of the housing would have a sort of cut-out.

In an example, shown in FIG. 1 as an option, the housing 18 is a flat detector housing. The display arrangement 14 comprises at least one flat display that is mounted on the housing. In addition, or alternatively, the at least one flat display is integrated in the outer part of the housing.

In an example, the housing structure is configured to be arranged above a subject support surface. The camera(s) is(are) mounted to the lower side of the detector and the display(s) on the upper side.

In an example, shown in FIG. 1 as an option, the camera arrangement 12 comprises at least one optical camera 24 mounted to the housing. For example, two or three or four cameras or more are provided.

In an example, the display arrangement comprises at least one display comprising at least one of the group of: an LCD screen, an LED screen and an OLED screen.

In an example, also shown in FIG. 1 as an option, it is further provided a user position detection arrangement 26 and a processing unit 28. The position detection arrangement 26 is configured to determine a spatial position of a user in relation to the housing. This is indicated with dotted detection lines 30. The processing unit 28 is configured to adapt the presentation based on the spatial position such that the presentation provides image data to the user of a situation hidden by the housing in the user's view. Hashed lines 32, 34 indicate the wireless or wire bound data and control connections.

The term "user" relates to a user operating the X-ray system or to a physician interacting with a subject. The term "subject" may also be referred to as individual. The "subject" may further also be referred to as patient, although it is noted that this term does not indicate whether any illness or disease is actually present with the subject.

Figure 2:
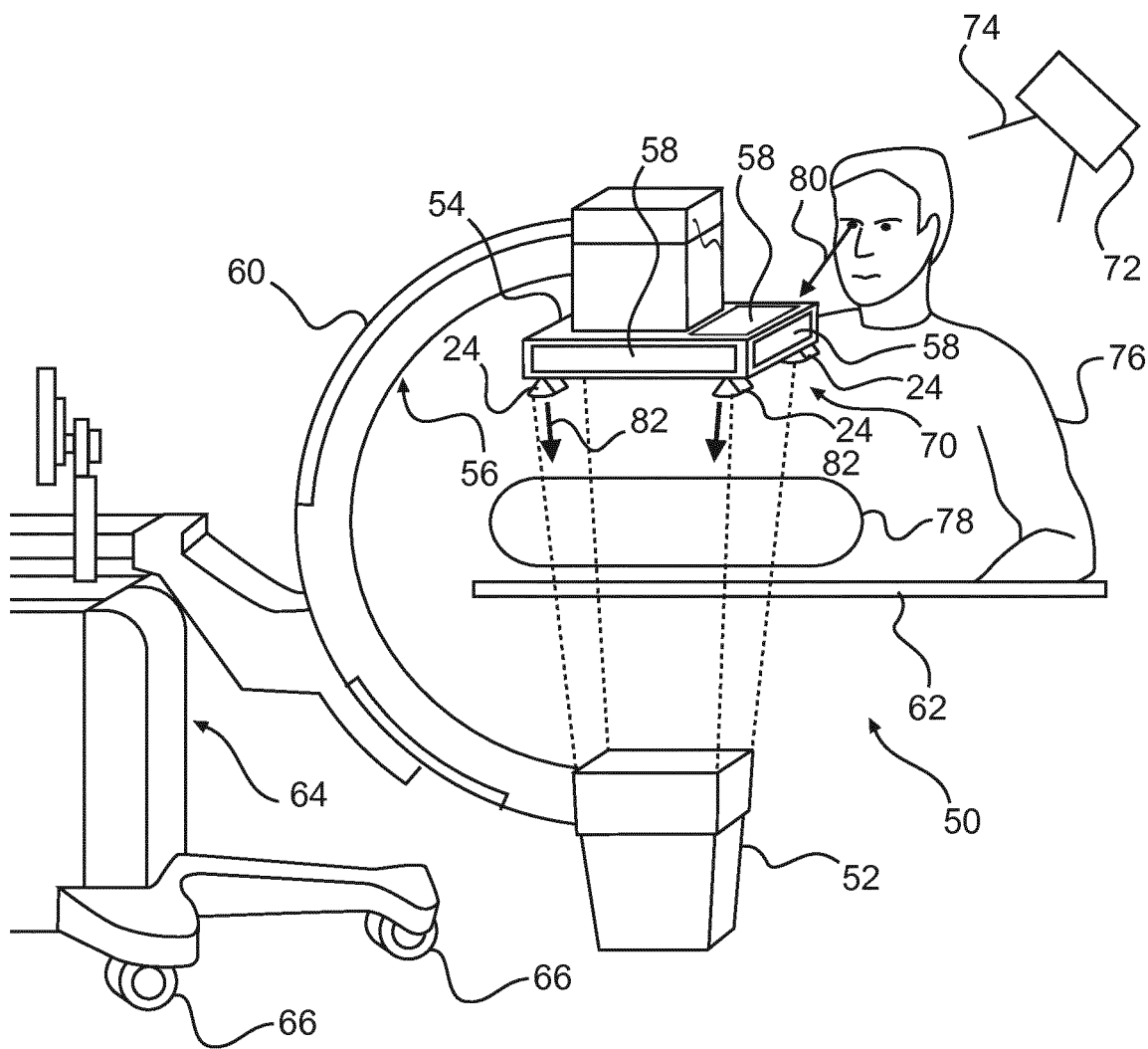
FIG. 2 shows an example of an X-ray imaging system with visual user guidance during X-ray imaging.

FIG. 2 shows an example of an X-ray imaging system 50 with visual user guidance during X-ray imaging. The system 50 comprises an X-ray source 52 and an X-ray detector 54. Further, a support structure 56 is provided and the guiding device 10 for visual guidance during X-ray imaging according to one of the preceding examples. The X-ray source 52 and the X-ray detector 54 are carried by the support structure 56. One of the X-ray source 52 and the X-ray detector 54 is arranged in the housing structure 16 of the guiding device 10. The first side 20 of the housing is facing towards the other one of the X-ray source 52 and the X-ray detector 54.

In an example, shown in FIG. 2 as an option, the X-ray detector 54 is arranged in the housing structure of the guiding device. The first side of the housing is facing towards the X-ray source 52.

In an example, the at least one camera has a viewing direction towards the X-ray source.

Figure 3:
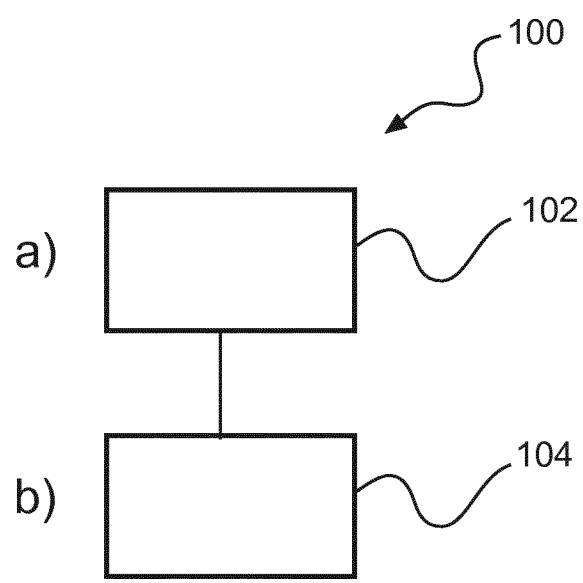
FIG. 3 shows steps of an example of a method for guiding a user during X-ray imaging.

In an example, shown in FIG. 3 as an option, the housing is provided with display segments 58 on lateral facing surface portions and also on upper surface portions.

The housing is equipped with display segments, or display elements, on surfaces that face a user when the detector is e.g. in an upright position for detecting X-rays generated in an area below a subject support 62. For example, flexible display elements are attached on a rounded or curved housing of the detector.

In an example, shown in FIG. 2 as an option, the support structure comprises a movable C-arm 60. Further, the X-ray source and the X-ray detector are mounted to opposing ends of the movable C-arm.

In another example, shown in FIG. 2 as an option, the C-arm 60 is arrangeable such that the X-ray source 52 is provided below a subject support table 62 and the X-ray detector 54 is provided above the subject support table 62.

In an example, shown in FIG. 2 as an option, the X-ray imaging system 50 is a mobile system comprising a base 64 with wheels 66. The movable C-arm 60 is movably mounted to the base 64.

As an option, a plurality of cameras 70 is provided mounted to the housing. Further, a spatial tracking arrangement 72 is provided that tracks the spatial relative positioning of the user, the detector and a region of interest. The tracking is schematically shown with lines 74. As indicated, the spatial tracking arrangement 72 is configured to determine a spatial relation between a user 76 and a subject 78 of interest, for example resting on the subject support table 62. The spatial tracking arrangement 72 is further configured to determine a user viewing direction 80, and to define a region of the subject of interest where a direct view is blocked by the housing. The spatial tracking arrangement 72 is also configured to select at least one of the plurality of the cameras 24 that has a viewing direction 82 that has a largest degree of similarity with the determined user viewing direction 80.

The tracking arrangement 72 may comprise head-mounted gear for the user to identify the user's position and orientation. Further, time of flight cameras may be provided to detect the spatial situation. The spatial situation may be detected and determined by optical means or by electromagnetic means.

FIG. 3 shows steps of an example of a method 100 for guiding a user during X-ray imaging. The method comprises the following steps:

In a first step 102, also referred to as step a), image data of a region of interest of a subject in front of the housing is captured with a camera arrangement mounted to a first side of a housing of a housing structure. The housing is a housing of an X-ray detector of an X-ray imaging system.

In a second step 104, also referred to as step b), the image data is presented as a live presentation of the region of interest with a display arrangement mounted to a second side of the housing, the second side being lateral and/or opposite to the first side; wherein a presentation is provided to a user on the second side of the housing, which presentation comprises live images from the first side.

For example, the live presentation comprises a sequence of live images.

In an example, steps a) and b) are provided in a continuous manner in parallel.

In another example, the steps a) and b) are provided in a repeated loop manner.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A guiding device for visual guidance during X-ray imaging, the guiding device comprising:
    a housing structure comprising a housing of an X-ray imaging system configured to house an X-ray detector;
    a camera arrangement configured to capture image data of a region of interest of a subject in front of the X-ray detector;

a display arrangement configured to present the captured image data as a live presentation of the region of interest, wherein the camera arrangement is mounted to the housing on a first side of the housing and the display arrangement is mounted to the housing on a second side of the housing, the second side being at least one of lateral to the first side or opposite to the first side, and wherein the display arrangement is configured to provide the live presentation from the first side of the housing to a user located on the second side of the housing; and a processor configured to adapt the live presentation based on a spatial relation between the user and at least one of the housing or the subject.

2. The guiding device according to claim 1,
wherein the housing is a flat detector housing; and
wherein the display arrangement comprises at least one flat display: i) mounted on the housing; or ii) integrated in an outer part of the housing.

3. The guiding device according to claim 1,
wherein the camera arrangement comprises at least one optical camera mounted to the housing; and
wherein the display arrangement comprises at least one display comprising at least one of an LCD screen, an LED screen, or an OLED screen.

4. The guiding device according to claim 1, further comprising:
a position detection arrangement configured to detect the spatial position of the user in relation to the at least one of the housing or the subject; and
wherein the processor is configured to adapt the live presentation based on the spatial position.

5. An X-ray imaging system with visual user guidance during X-ray imaging, the system comprising:
the guiding device for visual guidance during X-ray imaging according to claim 1;
an X-ray source and an X-ray detector carried by a support structure;
wherein the X-ray detector is arranged in the housing structure of the guiding device; and
wherein the first side of the housing is facing towards the X-ray source.

6. The system according to claim 5,
wherein the display arrangement is configured with display segments on lateral facing surface portions of the housing; and
wherein the display segments cover at least half of the lateral facing surface portions.

7. The system according to claim 5, wherein the display arrangement is configured to display the captured image data overlaid on the live presentation.

8. The system according to claim 5,
wherein the support structure comprises a movable C-arm; and
wherein the X-ray source and the X-ray detector are mounted to opposing ends of the movable C-arm.

9. The system according to claim 8, wherein the C-arm is arrangeable such that the X-ray source is provided below a subject support table and the X-ray detector is provided above the subject support table.

10. The system according to claim 8,
wherein the X-ray imaging system is a mobile system comprising a base with wheels; and
wherein the movable C-arm is movably mounted to the base.

11. The system m according to claim 5, further comprising:
a plurality of cameras mounted to the housing; and
wherein, to adapt the live presentation, the processor is further configured to:
determine a user viewing direction;
define a region of the subject where a direct view is blocked by the housing; and
select at least one of the plurality of the cameras that has a viewing direction that has a largest degree of similarity with the determined user viewing direction.

12. The guiding device according to claim 1, wherein the adapted presentation provides to the user image data of a situation hidden from the user's view by the housing.

13. A method for guiding a user during X-ray imaging, the method comprising:
capturing image data of a region of interest of a subject in front of a housing with a camera arrangement mounted to a first side of the housing, wherein the housing is configured to house an X-ray detector of an X-ray imaging system;
presenting the image data to a user as a live presentation of the region of interest by a display arrangement mounted to a second side of the housing, the second side being at least one of lateral to the first side or opposite to the first side; and
adapting the live presentation based on a spatial relation between the user and at least one of the housing or the subject.

14. The method according to claim 13, wherein adapting the live presentation further comprises:
detecting the spatial position of the user in relation to the at least one of the housing or the subject; and
adapting the live presentation based on the spatial position.

15. The method according to claim 13, wherein adapting the live presentation further comprises:
determining a user viewing direction;
defining a region of the subject where a direct view is blocked by the housing; and
selecting at least one of a plurality of cameras mounted to the housing with a viewing direction that has a largest degree of similarity with the determined user viewing direction.

16. The method according to claim 13, wherein the adapted presentation provides to the user image data of a situation hidden from the user's view by the housing.

\* \* \* \* \*